United States Patent

Bruna

[11] Patent Number: 5,988,496
[45] Date of Patent: Nov. 23, 1999

[54] DOSE COUNTER FOR INHALERS

[75] Inventor: Pascal Bruna, Rouen, France

[73] Assignee: Valois S.A., Le Neubourg, France

[21] Appl. No.: 08/765,104

[22] PCT Filed: Jun. 9, 1995

[86] PCT No.: PCT/FR95/00756

§ 371 Date: Feb. 13, 1997

§ 102(e) Date: Feb. 13, 1997

[87] PCT Pub. No.: WO95/34874

PCT Pub. Date: Dec. 21, 1995

[30] Foreign Application Priority Data

Jun. 10, 1994 [FR] France ................................ 94 07114

[51] Int. Cl.⁶ .............................. G06M 1/00; B67D 5/30
[52] U.S. Cl. ........................................ 235/91 R; 222/18
[58] Field of Search .................... 235/91 R, 115, 235/132 R; 222/32, 36, 18

[56] References Cited

U.S. PATENT DOCUMENTS

| | | | |
|---|---|---|---|
| 165,054 | 6/1875 | Baldwin . | |
| 3,227,127 | 1/1966 | Gayle | 116/121 |
| 3,297,198 | 1/1967 | Wright | 221/5 |
| 3,454,152 | 7/1969 | Immerman et al. | 206/42 |
| 3,495,567 | 2/1970 | Hayes et al. | 116/121 |
| 3,986,005 | 10/1976 | Itoh | 235/96 |
| 4,041,628 | 8/1977 | Sasson | 40/111 |
| 4,090,354 | 5/1978 | Schneiter | 58/117 |
| 4,532,415 | 7/1985 | Alway | 235/131 R |
| 4,565,302 | 1/1986 | Pfeiffer et al. | 222/38 |
| 4,756,423 | 7/1988 | Holtsch | 206/534 |
| 4,817,822 | 4/1989 | Rand et al. | 222/38 |
| 4,890,572 | 1/1990 | Huang | 116/298 |
| 4,945,521 | 7/1990 | Klaus | 368/21 |
| 5,261,548 | 11/1993 | Barker et al. | 215/230 |
| 5,285,427 | 2/1994 | Vaucher | 368/21 |
| 5,384,755 | 1/1995 | Feremczy | 368/35 |
| 5,482,030 | 1/1996 | Klein | 128/200.23 |
| 5,718,355 | 2/1998 | Garby et al. | 222/36 |

FOREIGN PATENT DOCUMENTS

| | | |
|---|---|---|
| 0254391 | 4/1988 | European Pat. Off. . |
| 819885 | 10/1937 | France . |
| 1514296 | 2/1968 | France . |
| 2103434 | 4/1972 | France . |
| 2341166 | 9/1977 | France . |
| 48610 | 9/1889 | Germany . |

Primary Examiner—Donald Hajec
Assistant Examiner—Daniel Sherr
Attorney, Agent, or Firm—Sughrue, Mion, Zinn, Macpeak & Seas, PLLC

[57] ABSTRACT

A device for counting doses of substance issued by a dispenser for fluids or powders, the device being characterized in that it comprises a first count wheel (10, 110) and a second count wheel (20, 120), both count wheels being mounted to rotate about a fixed axis of rotation (3, 103), the first count wheel (10, 110) comprising a set of teeth (11, 111) extending circumferentially about the fixed axis of rotation (3, 103) and co-operating with a drive member (30, 130) for rotating the first count wheel about the fixed axis of rotation on each use of the dispenser, the first count wheel (10, 110) further including a drive tongue (14, 114) that is movable between a rest position in which it does not co-operate with the second count wheel (20, 120), and a drive position in which it does co-operate with the second count wheel (20, 120) to cause it to rotate about the fixed axis of rotation, said drive tongue (14, 114) being forced into its drive position by cam (8, 108).

22 Claims, 5 Drawing Sheets

DOSE COUNTER FOR INHALERS

BACKGROUND OF THE INVENTION

The present invention relates to a device for counting doses issued by a substance dispenser, and more particularly by an inhaler of the kind used, for example, in the field of pharmacy.

In medical applications in particular, it is often necessary to spray some particular number of doses of substance contained in the dispenser, e.g. on a daily basis. To prevent mistakes in handling and/or dosage, it is desirable to provide means that serve to display the number of doses that have been sprayed, or that remain to be sprayed if the initial display gives the maximum number of doses that can be displayed (up-counter or down-counter).

Proposals have already been made, in patent EP-0 269 496 for a counter that counts actuation of the pushbutton and that comprises a count wheel mounted to rotate coaxially with the pushbutton and provided with a crown of axially extending peripheral teeth. A flexible blade secured to the pushbutton drives the wheel causing it to rotate when the pushbutton is actuated. That device is simple and cheap, but because it has only one wheel it is limited as to number of doses that can be counted.

Also, since that device transforms the axial motion of the pushbutton into rotary motion of the wheel, it is unsuitable for operating independently of the actuating pushbutton.

An object of the present invention is to provide a device for counting doses that is capable of counting an arbitrary number of doses (typically several tens to several hundreds of doses) and capable of being actuated by a member exerting movement in translation.

SUMMARY OF THE INVENTION

Another object of the present invention is to provide a device for counting doses that is capable of counting an arbitrary number of doses (typically several tens to several hundreds of doses) and that is capable of being actuated by a member exerting movement in rotation.

Another object of the invention is to provide a device for counting doses that is intended to count a predetermined number of doses and that is adapted to prevent the substance dispenser being actuated after said predetermined number of doses has been counted.

The present invention thus provides a device for counting doses of substance issued by a dispenser for fluids or powders, the device being characterized in that it comprises a first count wheel and a second count wheel, both count wheels being mounted to rotate about a fixed axis of rotation, said first count wheel comprising a set of teeth extending circumferentially about said fixed axis of rotation and co-operating with a drive member for rotating said first count wheel about said fixed axis of rotation on each use of the dispenser, said first count wheel further including a drive tongue that is movable between a rest position in which it does not co-operate with said second count wheel, and a drive position in which it does co-operate with said second count wheel to cause it to rotate about said fixed axis of rotation, said drive tongue being forced into its drive position by cam means.

More particularly, said second count wheel includes a set of teeth disposed circumferentially about said fixed axis of rotation and said drive tongue of said first count wheel includes a head at one end, said head engaging in said set of teeth of said second count wheel when said drive tongue is in its drive position.

Preferably, said first count wheel acts as a units counter and includes a peripheral set of teeth containing ten teeth, said ten teeth being uniformly distributed around said fixed axis, and each time said first count wheel has performed a complete revolution about said fixed axis of rotation said drive tongue co-operates with said cam means to rotate said second count wheel which acts as a tens counter.

Advantageously, there are provided a first locking device acting on the first count wheel to prevent it from returning in the direction opposite to the direction of rotation imposed by said drive element, and a second locking device acting on said second count wheel to prevent it from rotating in the direction opposite to the direction of rotation imposed by said drive tongue of said first count wheel.

More particularly, said second locking device comprises a flexible leg secured to said second count wheel and provided at its one of its ends with a stud, said stud co-operating with a grooved profile that is fixed relative to the axis of rotation to prevent said second count wheel from rotating in either direction when said drive tongue of said first count wheel is in its rest position. Any rotation of the second count wheel because of possible friction is thus avoided.

Advantageously, said fixed grooved profile which co-operates with said stud of said flexible leg of said second locking device includes fixed abutment means locking said stud of said flexible leg, thus preventing rotation of said second count wheel, the maximum number of doses issued by the dispenser thus being determined by the number of grooves in the grooved profile situated ahead of said abutment means.

Thus, a second count wheel having five teeth restricts the number of doses issued to forty-nine, whereas with twenty teeth the maximum number of doses issued would be one hundred ninety-nine.

In a first embodiment of the invention, a rod is mounted in fixed manner on said fixed axis of rotation and the first and second count wheels are substantially annular and are mounted to rotate on said fixed rod, said first count wheel having a peripheral set of teeth extending circumferentially about said fixed axis with the teeth thereof being outwardly directed, said set of teeth co-operating with a drive member secured to an actuator pushbutton of the dispenser and exerting movement in translation, said drive element co-operating on each actuation of the pushbutton with a tooth of said set of teeth to cause said first count wheel to rotate about said fixed axis or rotation.

Preferably, there is provided a first locking device including a fixed flexible blade which co-operates with the set of teeth of said first count wheel to prevent it from rotating in the direction opposite to the direction of rotation imposed by said drive member.

In the first embodiment of the invention, said first count wheel includes a drive tongue which extends circumferentially about said fixed axis of rotation and which includes a head at one end, the head being radially movable between a rest position in which said head extends radially inwards beyond the outer annular surface of the first count wheel, and a drive position in which the head co-operates with said second count wheel, said cam means being fixed relative to said axis of rotation and being disposed without friction substantially against said outer annular surface of said first count wheel level with said drive tongue to force said head of said drive tongue into its drive position each time said first count wheel has performed one complete revolution about said fixed axis of rotation.

Also, said second count wheel preferably includes a set of teeth extending circumferentially about said fixed axis of rotation and facing outwardly, said set of teeth being disposed radially inside said drive tongue of said first count wheel in such a manner that when said head of the tongue is in its drive position it engages in a tooth of said set of teeth to drive said second count wheel to rotate about said fixed axis of rotation. If said set of teeth of the second count wheel has only a few teeth (e.g. five), then it naturally occupies only a fraction of the circumference of said second count wheel.

Advantageously, the outside of said head of the drive tongue has a profile complementary to the profile of said fixed cam means, and the inside of said head has a profile that is complementary to the profile of said teeth of said set of teeth of the second count wheel.

In a second embodiment of the invention, said first count wheel includes a first set of teeth extending circumferentially about said fixed axis of rotation and having its teeth inwardly directed and uniformly distributed around said fixed axis to co-operate with a drive member exerting rotary movement, said drive member being actuated by the user by means of an actuator knob that is movable in rotation about the axis of rotation between first and second extreme positions.

Preferably, said drive member is annular, and mounted to rotate about said fixed axis of rotation, and includes an annular flexible arm movable radially between a rest position in which a projecting portion of said arm extends radially outwards beyond the annular outer surface of said arm, and a drive position in which said projecting portion of the arm co-operates with a tooth of said first set of teeth of said first count wheel to drive it in rotation, said flexible arm being forced into its drive position by the actuator knob.

Advantageously, said actuator knob is annular and is mounted to rotate about said fixed axis of rotation in such a manner as to surround said drive member, said actuator knob including means for rotating said drive member about said fixed axis of rotation, and means for forcing said arm into its drive position.

In particular, said means for forcing said arm into its drive position include a swelling disposed on the inner annular face of said actuator knob, and said means for rotating the drive member include two projections which co-operate with said drive member, both projections being disposed at the same height on the inner annular face of said actuator knob, the first projection being adapted to cause the drive member to rotate in one direction to bring the projecting portion of its arm face to face with a tooth of said first set of teeth, and the second projection being adapted to drive the drive member in the other direction to rotate said first count wheel when the flexible arm is in its drive position.

More precisely, said first set of teeth of said first count wheel has ten teeth, the angular distance between the two extreme positions of the actuator knob being about 180°, and said projections being disposed so as to be angularly spaced apart by about 144°, said actuator knob being initially rotated through 180° in one direction towards its second extreme position to bring said projecting portion of the arm of the drive member face to face with the next tooth in the first set of teeth and then being returned to its first extreme position by being rotated in the opposite direction, the second projection rotating said drive member, and said arm is forced into its drive position to cause said first count wheel to rotate about the axis of rotation.

In this second embodiment of the invention, said counter device further includes a full stroke device preventing said actuator knob from being returned to its initial position unless it has previously been rotated as far as its stop means, so as to ensure that said projecting portion of said arm is properly positioned facing a tooth of said first set of teeth.

Optionally, said full stroke device comprises a fixed plate secured to said fixed axis of rotation and supporting a substantially annular rail extending circumferentially about said axis of rotation through about 180°, and a pawl provided with a flexible finger, said pawl being constrained to rotate with said actuator knob, said flexible finger being constrained in the initial position of the actuator knob to pass inside said rail, said rail including a rack co-operating with said flexible finger to prevent said actuator knob rotating in an opposite direction, said flexible finger exiting said rail at an end thereof to enable said actuator knob to return to its initial position. Advantageously, said end of said rail forms stop means defining the second extreme position of said actuator knob.

Preferably, said first count wheel includes a second set of teeth extending circumferentially about said fixed axis of rotation and having its inwardly extending teeth uniformly distributed about said fixed axis of rotation to co-operate with a first locking device secured to a fixed tubular element fixedly mounted on said fixed axis of rotation and including at least one flexible element preventing said first count wheel from rotating in the direction opposite to the direction of rotation imposed by said drive member.

In the second embodiment of the invention, said drive tongue extends circumferentially about said fixed axis of rotation, its inner surface approximately forming an annular surface, and includes at one end a head that is radially movable between a rest position in which the head extends radially inwards beyond said inner annular surface and a drive position in which said head cooperates with said second count wheel, said cam means being secured to said fixed tubular element and disposed without significant friction against said inner annular surface of said drive tongue to force the head of said tongue into its drive position whenever said first count wheel has performed a complete revolution about said axis of rotation.

Advantageously, said second count wheel includes a set of teeth extending circumferentially about said fixed axis of rotation and directed inwardly, said set of teeth being disposed radially outside said drive tongue of said first drive wheel in such a manner that in its drive position said head of the tongue engages in one of the teeth of said set of teeth to drive said second count wheel in rotation about said fixed axis of rotation.

Preferably, the first and second count wheels include display means on their respective outer peripheral surfaces.

BRIEF DESCRIPTION OF THE FIGURES

Other characteristics and advantages of the present invention appear from the following detailed description of two embodiments given by way of non-limiting example and with reference to the accompanying drawings.

In the drawings.

DETAILED DESCRIPTION OF THE PREFERRED EMBODIMENTS

Figure 1:
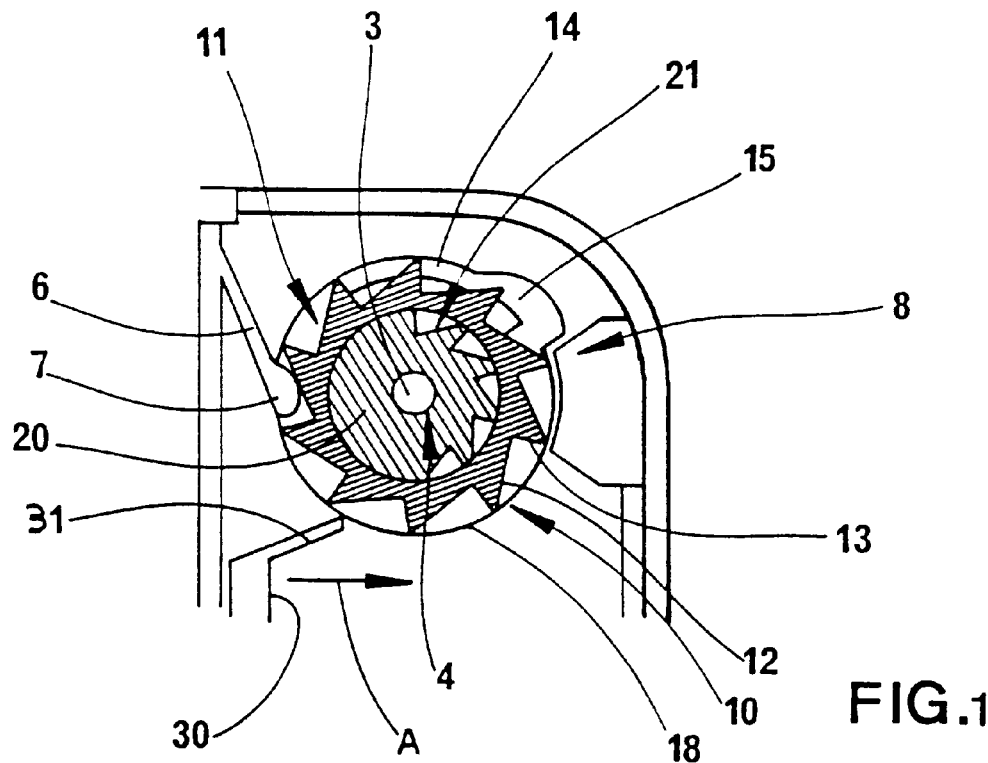
FIG. 1 is a diagrammatic cross-section view of a counter device constituting a first embodiment of the invention.
Figure 2:
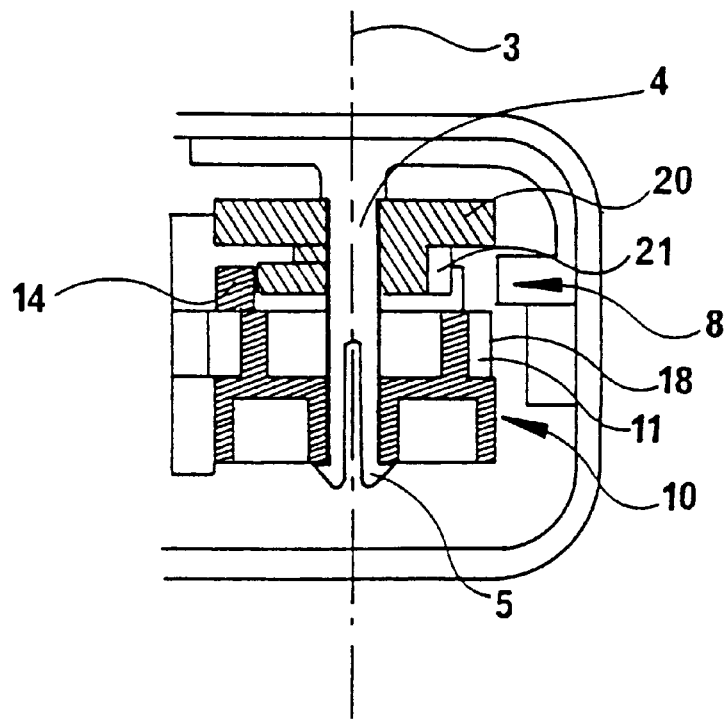
FIG. 2 is a cross-section view on a plane perpendicular to the section of FIG. 1, showing the FIG. 1 counter device.

FIGS. 1 to 5 show a first embodiment of the counter device of the invention which is adapted to count actuations of the pushbutton of a substance dispenser. In this embodiment, the device transforms a translation movement of the pushbutton into a rotary movement of the count wheel(s).

The counter device comprises a first count wheel 10 and a second count wheel 20. According to the invention, these two count wheels 10 and 20 are mounted to rotate about a common fixed rotary axis 3, a rod 4 being mounted in fixed manner along said rotary axis 3 to support said count wheels. Advantageously, the fixed rod 4 may include securing means 5 at its end to prevent any translational displacement of said count wheels 10, 20 along said rod 4.

Figure 3:
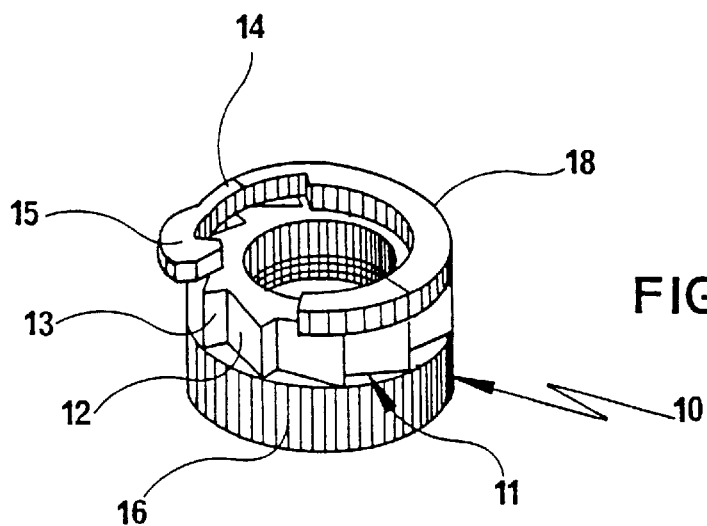
FIG. 3 is a perspective view of the first count wheel of the device shown in FIGS. 1 and 2.

According to the invention, the first count wheel 10 has a set of teeth 11 disposed circumferentially about said axis of rotation 3. As shown in FIGS. 1 and 3, said count wheel 10 is preferably substantially annular and said set of teeth 11 lies on its periphery with the teeth extending outwards. Thus, the teeth 11 can co-operate with a drive member 30 disposed tangentially to said first wheel 10 and, for example, secured to the pushbutton of the dispenser (not shown). This drive member 30 advantageously includes an end 31 of shape adapted to engage in a tooth of said set of teeth 11.

Preferably, said set of teeth 11 comprises exactly ten teeth, and the first count wheel 10 thus acts as a units counter.

As shown in FIGS. 1 and 3, the teeth of said set 11 are all identical and each comprises a sloping bottom wall 12 extending approximately circumferentially relative to the axis of rotation 3 and an abutment wall 13 that is approximately perpendicular to said bottom wall 12 and thus extends approximately radially relative to said axis 3. In operation, the end 31 of the drive member 30 engages along said bottom wall 12 in the direction of arrow A of FIG. 1 so as to come into abutment against the abutment wall 13, thereby rotating the first count wheel 10 about the axis of rotation 3 by exerting thrust on said abutment wall 13. When the pushbutton (not shown) and thus the drive member 30 return to their rest position, the end 31 of said drive member slides along said bottom wall 18 in the direction opposite to arrow A and takes up a position facing the next tooth in said set 11. Advantageously, the end 31 is resilient so as to provide little resistance, e.g. due to friction, as the drive member 30 returns to its rest position. The drive member 30 is preferably disposed in such a manner that on each actuation it causes the first count wheel 10 to rotate through an angle corresponding to exactly one tooth of the set 11.

In order to prevent the first count wheel 10 from being rotated backwards due to possible friction against said end 31 of the drive member 30 against the bottom wall 12 of one of the teeth of the set of teeth 11 while the drive member 30 is returning to its rest position, a first locking device 6 is provided that acts on the set of teeth 11.

The locking device advantageously comprises a flexible blade 6 that is fixed relative to said axis of rotation 3, with the end 7 thereof engaging in the set of teeth 11. Because said blade 6 is flexible, when the wheel 10 is rotated by the drive member 30, it slides over the bottom wall 12 of the tooth with which it is engaged and clicks into the following tooth.

This click action can present several advantages.

Firstly, because of the flexibility of the blade, it makes a small noise which is useful in informing the user that the count wheel 10 has been advanced by one unit. Secondly, in powder inhalers where the dose of substance drops into the metering chamber under gravity, the clicking of the blade 6 generates a small amount of vibration that can favor refilling of said metering chamber.

Naturally, by pressing against the abutment wall 13 of the corresponding tooth and as can be seen clearly in FIG. 1, the end 7 of the blade 6 prevents the count wheel 10 from returning in the direction opposite to the direction of rotation imparted by the drive member 30.

The first count wheel 10 also includes its own drive tongue 14 for rotating the second count wheel 20. This tongue 14 preferably extends circumferentially about said fixed axis of rotation 3 and it is movable radially between a rest position and a drive position. Advantageously, this mobility is provided by said tongue 14 being somewhat flexible.

As shown in FIG. 3, the drive tongue extends over a fraction of the periphery of the first count wheel 10 and it includes a head 15 at one of its ends. In the rest position of the tongue 14 its head 15 extends radially outwards beyond the outer annular surface 18 of said first count wheel 10 and it does not co-operate with the second count wheel 20. In the drive position of the tongue 14, its head 15 co-operates with said second wheel 20 to rotate it about said axis of rotation 3.

According to the invention, the tongue 14 is forced into its drive position by cam means 8. The cam means 8 is preferably fixed relative to the axis of rotation 3 and may advantageously be secured to the rod 4 which supports both count wheels 10 and 20. It is disposed substantially without friction against said outer annular surface 18 of the first count wheel, and specifically level with the drive tongue 14. Thus, each time the first count wheel performs one complete revolution about the axis of rotation 3, the head 15 of the tongue goes past said cam means 8 and is forced into its drive position. In the embodiment shown in the FIGS. 1 and 2, the cam means 8 has a rounded profile facing the tongue 14 and matching the outer annular surface 18 of the first count wheel 10, said profile extending over a length that corresponds to about the angular length of one tooth of the set of teeth 11. The head 15 of the drive tongue 14 has a profile on its outside that is complementary to that of said cam means 8, and on its inside it has a profile that is complementary to the teeth of the set of teeth 11. It is thus ensured that the drive tongue 14 is forced into its drive position once only during each complete revolution of the first counting tooth wheel 10, and that this occurs only over an angular distance corresponding to one of the ten teeth in the set 11. The first count wheel 10 thus properly performs its function of counting units.

Figure 4A:
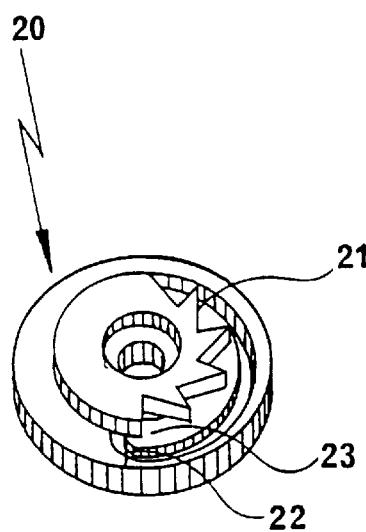
FIGS. 4a and 4b are perspective views in two different directions of the second count wheel of the device of FIGS. 1 and 2.
Figure 4B:
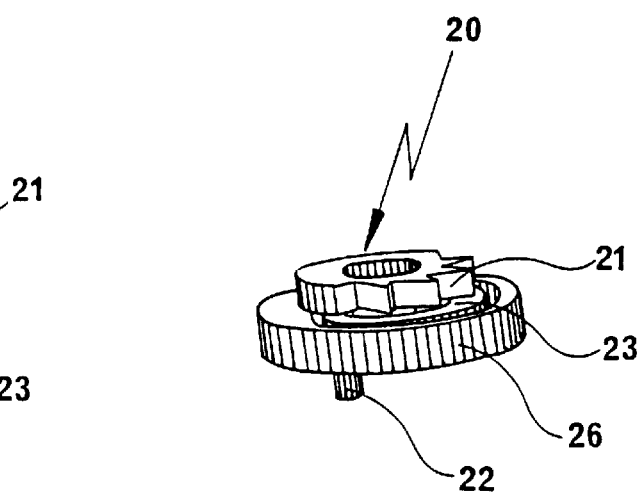
Figure 6:
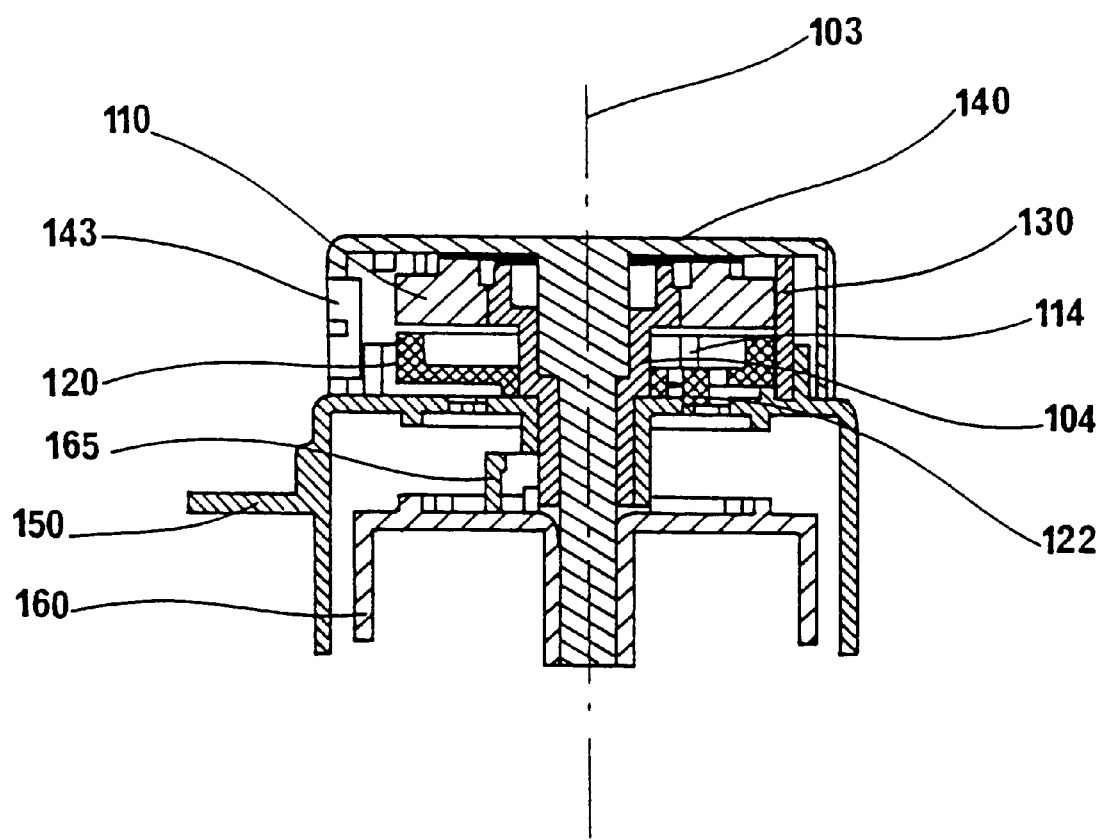
FIG. 6 is a diagrammatic cross-section view through a counter device constituting a second embodiment of the invention.

The second count wheel 20 is shown in detail in FIGS. 4a and 4b. It is generally substantially annular in shape and, like the first wheel 10, it is engaged on the fixed rod 4 about which it can rotate, but along which it is not free to slide. According to the invention, this second count wheel 20 has a set of teeth 21 disposed circumferentially relative to the axis of rotation 3. Advantageously, this set of teeth 21 is offset radially inwards towards the axis of rotation 3 such that when mounted on said fixed rod 4, said set of teeth 21 of the second count wheel 20 is disposed radially inside said drive tongue 14 of the first count wheel. Preferably, both wheels rotate relative to each other with a small amount of friction. Thus, when the head 15 of the drive tongue 14 is forced radially into its driving position, it engages with one of the teeth of said set of teeth 21 of the second count wheel 20 so as to rotate it. Advantageously, the teeth of said second set of teeth 21 are substantially similar in shape to the teeth of the first wheel 10 so as to co-operate effectively with the head 15 of the tongue 14. Preferably, the angular offset between two successive teeth of said set of teeth 21 of the second wheel 20 is identical to the angular offset between two successive teeth in the set 11 of the first wheel 10. In this way, on each revolution, the driving tongue 14 in its driving position serves to advance the second count wheel 20 by exactly one tooth. The second wheel 20 thus acts as a tens counter while the first wheel 10 acts as a units counter.

Figure 5:
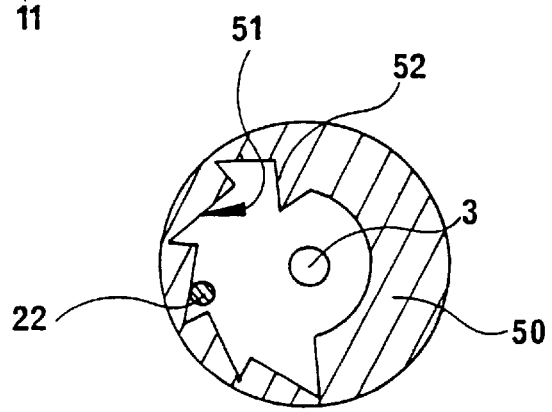
FIG. 5 is a diagrammatic horizontal section through the second non-return device in the first embodiment.

In order to prevent the second count wheel 20 from rotating in the direction opposite to the direction in which it is rotated by said drive tongue 14 of the first count wheel 10, a second locking device is provided. Advantageously, said locking device comprises a locking plate 50 that is fixed relative to the axis of rotation 3, said locking plate 50 being designed to co-operate with a stud 22 integral with the second count wheel 20. Said locking plate 50 preferably supports a grooved profile 51 with grooves that extend circumferentially about axis of rotation 3. As shown in FIG. 5, the groove profile 51 may face inwards, but it could equally well face outwards. In addition, the grooves shown in FIG. 5 are similar in shape to the teeth, but they could have any other shape suitable for releasably retaining said stud 22 of the second count wheel 20. Thus, the grooved profile 51 not only prevents the second count wheel 20 from rotating in the direction opposite to the direction of rotation imposed by the tongue 14, but it also prevents any rotation in the direction of rotation imposed by the tongue 14 while said tongue is in its rest position. Such friction as may exist between the first and second count wheels 10 and 20 therefore does not give rise to rotation of the second count wheel 20. Advantageously, said grooved profile 51 has a number of grooves identical to the number of teeth in the set of teeth 21 of the second count wheel 20. At its end corresponding to the last groove, it may also include abutment means 52 preventing said stud 22 from rotating, and consequently preventing the second wheel 20 from continuing its rotation. When the second wheel 20 can no longer rotate, it locks the first wheel 20 at the moment when the tongue 14 is forced into its drive position. If, as is preferable, dose counting is driven by actuating the dispenser, then said abutment means 52 also locks actuation of the dispenser. The maximum number of doses that can be issued by the dispenser is thus determined by the number of grooves in said grooved profile 51 situated ahead of said abutment means 52 (in the direction of rotation corresponding to counting). The stud 22 secured to the second count wheel 20 is preferably fixed at the end of a flexible leg 23 of said second wheel which extends circumferentially about the axis of rotation 3. Because of the radial flexibility of the leg 23, the stud 22 can thus be urged towards the following groove of the grooved profile 51 while the second wheel 20 is being rotated by the drive tongue 14 of the first wheel 10.

The first and second count wheels preferably include display means such as digits enabling the user to be informed either of the number of doses that have been issued or else of the number of doses that remain to be issued. Advantageously, this display is situated on the outer peripheral surfaces 16 and 26 of the first and second count wheels 10 and 20 respectively. Thus, the first count wheel 10 has the digits 0 to 9 distributed around its periphery with each digit corresponding to one tooth in the set 11. In the example shown in FIGS. 1 to 5, the second count wheel has five teeth, and the maximum number of doses that the dispenser can issue is thus forty-nine. It is naturally possible to fix some other maximum number of doses by providing a different number of teeth for the second count wheel.

FIGS. 6 to 9 show a second embodiment of the invention. This second embodiment relates to a counter device which is actuated by means of a drive member that exerts rotary movement. For example, there exist inhalers comprising a compressed air mechanism for expelling doses of substance from the metering chamber, said metering chamber being filled by rotary filling means. In this case, the filling of the metering chamber is not directly tied to actuating the expulsion mechanism.

Since the expulsion mechanism can be actuated only after the metering chamber has indeed been filled, it is advantageous in this kind of dispenser to count the number of times the metering chamber has been filled.

The counter device of this second embodiment of the invention comprises first and second count wheels 110 and 120 mounted to rotate freely about a fixed axis of rotation 103.

Figure 7:
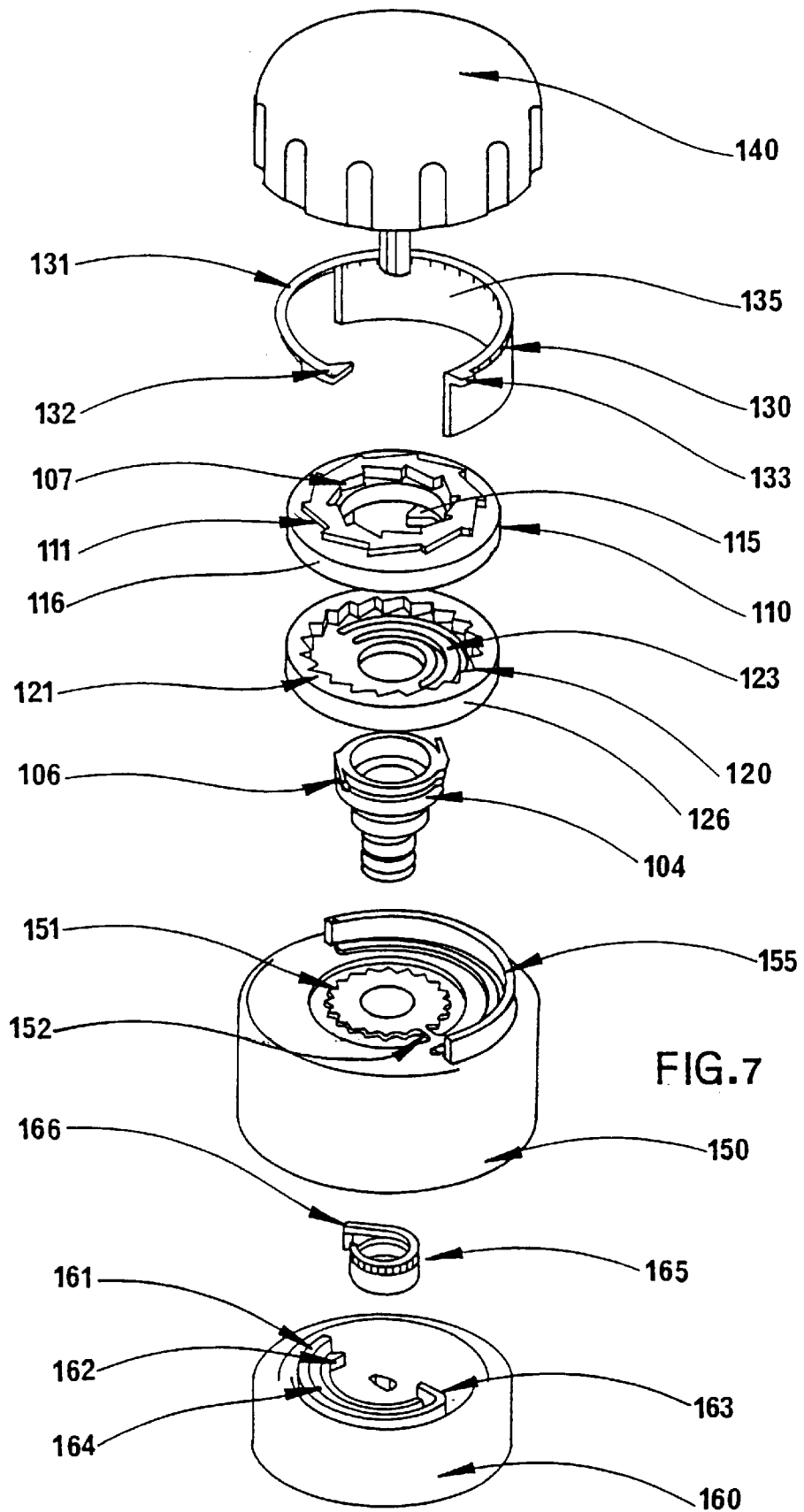
FIG. 7 is an exploded view of the FIG. 6 device.
Figure 8:
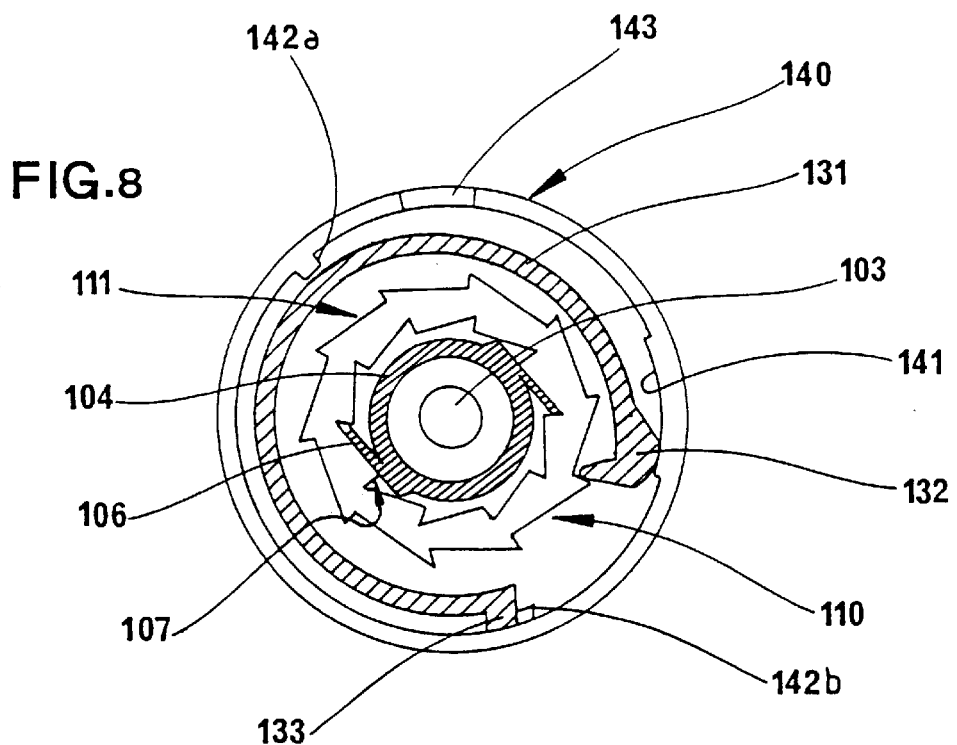
FIG. 8 is a cross-section view of the device of FIGS. 6 and 7 on a plane perpendicular to the section of FIG. 6 and showing, in particular, the first count wheel.

Advantaously, a fixed tubular element 104 is mounted along said axis of rotation 103 to support both count wheels 110 and 120 so that they can rotate freely. As described for the first embodiment, the first count wheel 110 is rotated about the fixed axis of rotation 103 by a drive member 130 which co-operates with a first set of teeth 111 of said first wheel 110. This first set of teeth 111 extends circumferentially around said axis of rotation 103 and comprises exactly ten teeth when the first wheel 110 acts as a units counter. Advantageously, the teeth of this first set 111 are all identical, being uniformly distributed over the entire circumference, and they are directed outwards. The drive member 130 is annular and is mounted to rotate about said axis 103 so as to surround said first count wheel 110. It has an annular flexible leg 131 extending circumferentially about said axis of rotation 103 and radially movable between a rest position and a drive position, said arm 131 being secured to an annular wall element 135 which advantageously extends over about half the circumference of the drive member 130. In its rest position where the arm 131 of the drive member 130 is not co-operating with the set of teeth 111 of the first wheel 110, a projecting portion 132 of said arm extends beyond the outer annular surface formed by the outside wall of said arm 131. Advantageously, this projecting portion 132 corresponds to one end of the arm 131 as shown in FIGS. 7 and 8. In its driving position, said projecting portion 132 co-operates with the set of teeth 111 of the first wheel 110 to drive it in rotation about the axis of rotation 103.

The device also includes an actuator knob 140 turned by the user. By way of example, and as described above, this actuator knob serves to fill the metering chamber of the dispenser. In the present embodiment of the invention, the actuator knob 140 is also annular and is mounted to rotate about the axis of rotation 103 so as to surround the drive member 130 and in particular so as to surround the flexible arm 131 thereof. The knob includes means 142 for rotating said drive member 130 about said axis of rotation 103, and means 141 for forcing said arm 131 of said drive member 130 into its drive position. It also includes a window 143 in its side wall to enable the user to see the number of doses that have been issued or that remain to be issued. As for the above-described first embodiment, the display is advantageously situated on the outer peripheral surfaces 116 and 126 of the first and second count wheels 110 and 120 respectively.

Advantageously, said means for rotating the drive member comprise two projections 142a and 142b situated on the inner annular face of the actuator knob 140. They co-operate with said drive member, e.g. via the flexible arm 131. Likewise, the means for forcing the arm 131 into its drive position are also disposed on the inside face of the actuator knob 140 and may be implemented, for example, in the form of a swelling 141 that projects inwards from said actuator knob.

The device operates as follows.

In the rest position of the counter device, the assembly constituted by the actuator knob 140, the drive member 130, and the first count wheel 110 is in a position corresponding to the final position of the procedure of counting the preceding dose. Thus, the projecting portion 132 of the flexible arm 131, e.g. a first end of said arm, is forced into its drive position by the swelling 141, the actuator knob 140 which is movable between two end positions that are preferably separated by a distance corresponding to rotation through about 180°, being in its first end position in which it can rotate only in one direction, e.g. counterclockwise as shown in FIG. 8. The second projection 142b is in contact with the second end 133 of the arm 131 and the first projection 142a is advantageously offset from the second projection 142b by a distance corresponding to an angle of about 144°.

Thus, when the user actuates the device, the actuator knob 40 is rotated in a forwards direction. The swelling 141 is no longer in contact with the projecting portion 132 of the flexible arm 131 and said arm therefore resiliently returns to its rest position in which it no longer co-operates with the first count wheel 110. Simultaneously, the second projection 142b disengages from the second end 133 of the arm 131. After rotating through about 144°, the first projection 142a comes to bear against said second end 133 of the arm 131. Continued rotation of the actuator knob 140 therefore causes the drive member 130 to rotate. Since the maximum rotation of the actuator knob 140 is about 180°, the drive member 130 which is still in its rest position therefore turns through a distance corresponding to an angle of about 36° which corresponds to exactly one tooth in the set 111 of the first count wheel 110. At the end of the stroke of the actuator knob 140, the projecting portion 132 of the arm 131 of the drive member is thus positioned facing the next tooth in the set 111. When the actuator knob reaches it second extreme position after rotating through about 180°, the user brings it back to its initial position by rotating it in the opposite direction, i.e. in the clockwise direction in the example shown in FIG. 8. After rotation through −144°, the second projection 142b comes once again into abutment against the end 133 of the flexible arm 131 and simultaneously the swelling 141 co-operates with the projecting portion 132 of said flexible arm to force said arm into its drive position. The projecting portion 132 is thus engaged with a tooth in the set of teeth 111 and continued rotation of the drive knob 140 causes said first count wheel 110 to rotate. After the actuator knob 140 has been rotated through −180° from its second extreme position, said actuator knob is back in its first extreme position and the count procedure has terminated.

The first count wheel is thus rotated about the axis of rotation 103 through an angle of about −36°, which corresponds to the spacing between two successive teeth in the set of teeth 111.

Advantageously, a full stroke device is provided to prevent the actuator knob 140 from being returned to its first extreme position before it has reached its second extreme position. This ensures that the projecting portion 132 of the arm 131 is accurately positioned in front of the following tooth in the set 111. This device advantageously includes a plate 160 which is fixed relative to the axis of rotation 103 and a pawl 165 constrained to rotate with the actuator knob 140, i.e. whose angular position depends on rotation thereof. The plate 160 supports a rail 161 which extends circumferentially about said axis of rotation 103 over about 180°. This rail 161 has at its inlet a flared inside wall portion 162, at its outlet an abutment wall 163, and between these two ends a rack 164 with axially-extending teeth. The pawl 165 has a flexible finger 166 which, in the rest position of the device, i.e. in the first extreme position of the actuator knob 140, is disposed inside the flared wall portion 162 of the rail 161.

When the actuator knob 140 is rotated, said flexible finger 166 is urged into the rail 161 by the flared wall portion 162 and co-operates with said rack 164. The teeth of said rack 164 are such that the flexible finger 166 can pass from one tooth to the next when the actuator knob 140 is rotated towards its second extreme position, but cannot pass from one tooth to the next when it is rotated towards its first extreme position. It is therefore not possible to return the actuator knob 140 to its initial position before reaching the outlet 163 of the rail 161. At the outlet of the rail, the flexible finger 166 disengages from the rack and returns resiliently to its relaxed position outside the rail 161. The actuator knob 140 can then be returned to its first extreme position to finish off the count procedure. Optionally, automatic return means such as a spring for example could return the actuator knob automatically to its first extreme position.

A first locking device is provided to prevent the first count wheel 110 from rotating in the direction opposite to the direction of rotation imposed by the drive member 130. This first locking device advantageously includes at least one flexible element 106 secured to the fixed tubular element 104 and engaging with a second set of teeth 107 on the first count wheel 110. This second set of teeth 107 is concentric with the first set of teeth 111 but its teeth face inwards to co-operate with the flexible element 106.

The interaction between the first and second count wheels is substantially identical to that of the first embodiment of the invention as described above. The only difference is that the set of teeth 121 of the second count wheel 120 has its teeth facing inwards, and the drive tongue 114 of the first count wheel 140 is forced into its drive position where its head 115 engages with one of the teeth of said set of teeth 121 by cam means 108 that is fixed relative to the axis of rotation 103 and secured to the fixed tubular element 104. The head 115 of the tongue 114 thus extends in the rest position radially inwards beyond the inner annular surface 118 of said tongue 114, and said cam means 108 is disposed without significant friction against said inner annular surface 118. When the head 115 passes over the cam means 108, the cam means force the head radially outwards to enable it to engage with the set of teeth 121 of the second count wheel 120.

As in the first embodiment, the second count wheel 120 includes a second locking device. This second locking device likewise comprises a grooved profile 151 supported by a cover 150 which is fixed relative to the axis of rotation 103 and which co-operates with a stud 122 secured to a flexible leg 123 of said second wheel 120. The operation of this second locking device is similar to that described above with reference to the first embodiment.

Figures 9A, 9B:
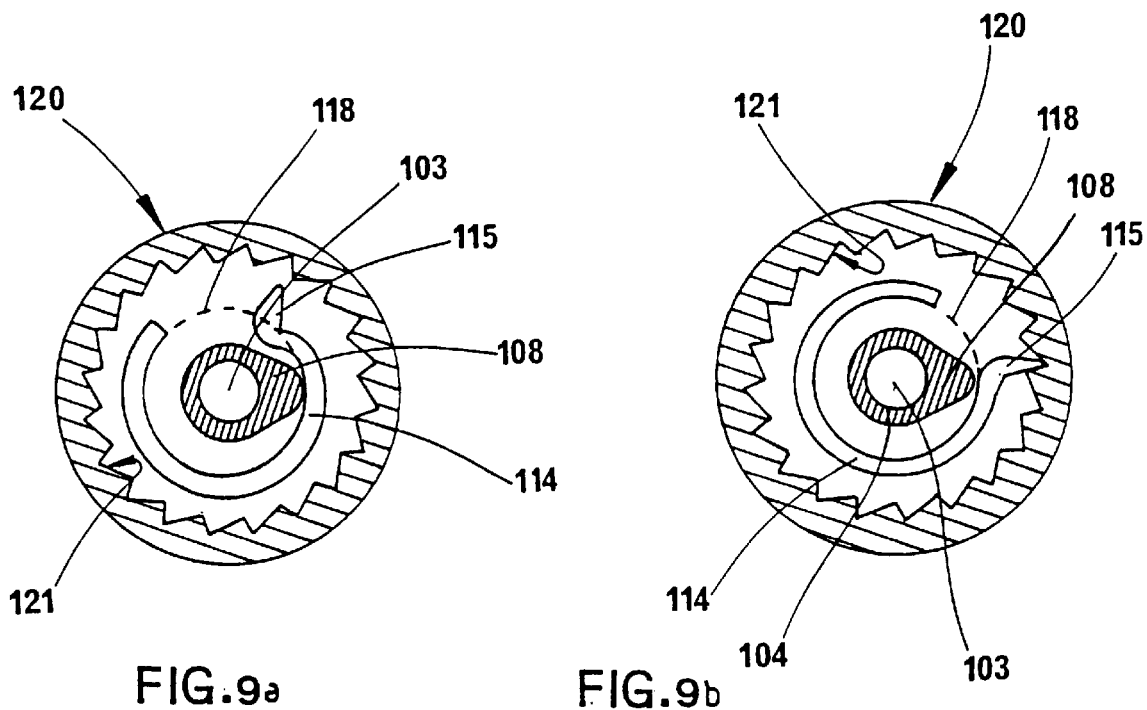
FIGS. 9a and 9b are cross-section views similar to that of FIG. 8 showing the second count wheel respectively with the driving tongue in its rest position and in its driving position.

In the example shown in FIGS. 7 and 9, the second count wheel 120 and the grooved profile 151 respectively comprise twenty teeth and twenty grooves. This counter is therefore adapted to counting 199 doses of substance. Advantaously, the cover 150 may also support a guide 155 for the actuator knob 140 and the wall element 135 of the drive member 130, said guide defining both extreme positions of said knob 140.

This second embodiment of the invention has been described with reference to FIGS. 6 to 9 which show one example thereof. It is clear that the device would also operate with an actuator knob that rotates through more or less than half a turn between its two extreme positions. For that purpose it suffices to adapt the offset between the two projections 142a and 142b and the positioning of the swelling 141 in order to achieve the same result. Similarly, it is possible to design a device operating with opposite directions of rotation.

The first and second count wheels (10, 110; 20, 120) are preferably single pieces of strong plastics material, thereby making them strong and reliable, and eliminating any risk of deterioration, in particular of their flexible and resilient portions.

I claim:

1. A device for counting doses of substance issued by a dispenser for fluids or powders, the device comprising a first count wheel (10; 110) and a second count wheel (20; 120), both of said count wheels being mounted to rotate about a fixed axis of rotation (3; 103), said first count wheel comprising a set of teeth (11; 111) extending circumferentially about said fixed axis of rotation and co-operating with a drive member (30; 130) for rotating said first count wheel about said fixed axis of rotation on each use of the dispenser, said first count wheel further including a drive tongue (14; 114) movable between a rest position in which it does not co-operate with said second count wheel, and a drive position in which it does co-operate with said second count wheel to cause it to rotate about said fixed axis of rotation, said drive tongue being forced into its drive position by cam means (8; 108), a first locking device (6; 106) acting on the first count wheel to prevent it from returning in the direction opposite to the direction of rotation imposed by said drive element, and a second locking device (23, 51; 123, 151) acting on said second count wheel to prevent it from rotating in either direction when said drive tongue of said first count wheel is in its rest position, wherein said second count wheel co-operates, after issuing a predetermined number of doses, with fixed abutment means (52; 152) which prevent any subsequent rotation of said second count wheel.

2. A counter device according to claim 1, in which said second count wheel (20, 120) includes a set of teeth (21, 121) disposed circumferentially about said fixed axis of rotation (3, 103) and said drive tongue (14, 114) of said first count wheel (10, 110) includes a head (15, 115) at one end, said head engaging in said set of teeth (21, 121) of said second count wheel when said drive tongue is in its drive position.

3. A counter device according to claim 1, in which said first count wheel (10, 110) acts as a units counter and includes a peripheral set of teeth (11, 111) containing ten teeth, said ten teeth being uniformly distributed around said fixed axis (3, 103), and each time said first count wheel has performed a complete revolution about said fixed axis of rotation said drive tongue (14, 114) co-operates with said cam means (8, 108) to rotate said second count wheel (20, 120) which acts as a tens counter.

4. A counter device according to claim 1, in which said second locking device comprises a flexible leg (23, 123) secured to said second count wheel and provided at one of its ends with a stud (22, 122), said stud co-operating with a grooved profile (51, 151) that is fixed relative to the axis of rotation.

5. A counter device according to claim 4, in which said fixed grooved profile (51, 151) which co-operates with said stud (22, 122) of said flexible leg (23, 123) of said second locking device includes fixed abutment means (52, 152) locking said stud (22, 122) of said flexible leg, thus preventing rotation of said second count wheel, the maximum number of doses issued by the dispenser thus being determined by the number of grooves in the grooved profile situated ahead of said abutment means (52, 152).

6. A counter device according to claim 1, in which a rod (4) is mounted in fixed manner on said fixed axis of rotation (3) and the first and second count wheels (10, 20) are substantially annular and are mounted to rotate on said fixed rod (4), said first count wheel (10) having a peripheral set of teeth (11) extending circumferentially about said fixed axis (3) with the teeth thereof being outwardly directed, said set of teeth (11) co-operating with a drive member (30) secured to an actuator pushbutton of the dispenser and exerting movement in translation, said drive element (30) co-operating on each actuation of the pushbutton with a tooth of said set of teeth (11) to cause said first count wheel (10) to rotate about said fixed axis or rotation (3).

7. A counter device according to claim 6, in which there is provided a first locking device including a fixed flexible blade (6) which co-operates with the set of teeth (11) of said first count wheel (10) to prevent it from rotating in the direction opposite to the direction of rotation imposed by said drive member (30).

8. A counter device according to claim 6, in which said first count wheel (10) includes a drive tongue (14) which extends circumferentially about said fixed axis of rotation (3) and which includes a head (15) at one end, the head being radially movable between a rest position in which said head (15) extends radially inwards beyond the outer annular surface (18) of the first count wheel (10), and a drive position in which the head (15) co-operates with said second count wheel (20), said cam means (8) being fixed relative to said axis of rotation (3) and being disposed without friction substantially against said outer annular surface (18) of said first count wheel (10) level with said drive tongue (14) to force said head (15) of said drive tongue (14) into its drive position each time said first count wheel (10) has performed one complete revolution about said fixed axis of rotation (3).

9. A counter device according to claim 8, in which said second count wheel (20) includes a set of teeth extending circumferentially about said fixed axis of rotation (3) and facing outwardly, said set of teeth being disposed radially inside said drive tongue (14) of said first count wheel in such a manner that when said head (5) of the tongue (14) is in its drive position it engages in a tooth of said set of teeth to drive said second count wheel (20) to rotate about said fixed axis of rotation (3).

10. A counter device according to claim 9, in which the outside of said head (15) of the drive tongue (14) has a profile complementary to the profile of said fixed cam means (8), and the inside of said head (15) has a profile that is complementary to the profile of said teeth of said set of teeth of the second count wheel (20).

11. A counter device according to claim 1, in which said first count wheel (110) includes a first set of teeth (111) extending circumferentially about said fixed axis of rotation (103) and having its teeth inwardly directed and uniformly distributed around said fixed axis (103) to co-operate with a drive member (130) exerting rotary movement, said drive member (130) being actuated by the user by means of an actuator knob that is movable in rotation about the axis of rotation (103) between first and second extreme positions.

12. A counter device according to claim 11, in which said drive member (130) is annular, and mounted to rotate about said fixed axis of rotation (103), and includes an annular flexible arm (131) movable radially between a rest position in which a projecting portion (132) of said arm (131) extends radially outwards beyond the annular outer surface of said arm (131), and a drive position in which said projecting portion (132) of the arm (131) co-operates with a tooth of said first set of teeth (111) of said first count wheel (110) to drive it in rotation, said flexible arm (131) being forced into its drive position by the actuator knob (140).

13. A counter device according to claim 12, in which said actuator knob (140) is annular and is mounted to rotate about said fixed axis of rotation (103) in such a manner as to surround said drive member (130), said actuator knob (140) including means (142) for rotating said drive member (130) about said fixed axis of rotation (103), and means (141) for forcing said arm (131) into its drive position.

14. A counter device according to claim 13, in which said means for forcing said arm (131) into its drive position include a swelling (141) disposed on the inner annular face of said actuator knob (140), and said means for rotating the drive member (131) include two projections (142a, 142b) which co-operate with said drive member (130), both projections (142a, 142b) being disposed at the same height on the inner annular face of said actuator knob (140), the first projection being adapted to cause the drive member (131) to rotate in one direction to bring the projecting portion (132) of its arm (131) face to face with a tooth of said first set of teeth (111), and the second projection (142b) being adapted to drive the drive member (130) in the other direction to rotate said first count wheel (110) when the flexible arm (131) is in its drive position.

15. A counter device according to claim 14, in which said first set of teeth of said first count wheel (110) has ten teeth, the angular distance between the two extreme positions of the actuator knob (140) being about 180°, and said projections (142a, 142b) being disposed so as to be angularly spaced apart by about 144°, said actuator knob (140) being initially rotated through 180° in one direction towards its second extreme position to bring said projecting portion (132) of the arm (131) of the drive member (130) face to face with the next tooth in the first set of teeth (111) and then being returned to its first extreme position by being rotated in the opposite direction, the second projection (142b) rotating said drive member (130), and in which said arm (131) is forced into its drive position to cause said first count wheel (110) to rotate about the axis of rotation (103).

16. A counter device according to claim 15, in which said counter device further includes a full stroke device preventing said actuator knob (140) from being returned to its initial position unless it has previously been rotated as far as its stop means, so as to ensure that said projecting portion (132) of said arm (131) is properly positioned facing a tooth of said first set of teeth (111).

17. A counter device according to claim 16, in which said full stroke device comprises a fixed plate (160) secured to said fixed axis of rotation (103) and supporting a substantially annular rail (161) extending circumferentially about said axis of rotation (103) through about 180°, and a pawl (165) provided with a flexible finger (166), said pawl (165) being constrained to rotate with said actuator knob (140), said flexible finger (166) being constrained in the initial position of the actuator knob to pass inside said rail, said rail (161) including a rack (164) co-operating with said flexible finger (166) to prevent said actuator knob (140) rotating in an opposite direction, said flexible finger (166) exiting said rail (161) at an end (163) thereof to enable said actuator knob (140) to return to its initial position.

18. A counter device according to claim 17, in which said end (163) of said rail (161) forms stop means defining the second extreme position of said actuator knob.

19. A counter device according to claim 11, in which said first count wheel (110) includes a second set of teeth (107) extending circumferentially about said fixed axis of rotation (103) and having its inwardly extending teeth uniformly distributed about said fixed axis of rotation (103) to co-operate with a first locking device secured to a fixed tubular element (104) fixedly mounted on said fixed axis of rotation (103) and including at least one flexible element (106) preventing said first count wheel (110) from rotating in the direction opposite to the direction of rotation imposed by said drive member (130).

20. A counter device according to claim 11, in which said drive tongue (114) extends circumferentially about said fixed axis of rotation (103), its inner surface approximately forming an annular surface (118), and includes at one end a head (115) that is radially movable between a rest position in which the head (115) extends radially inwards beyond said inner annular surface (118) and a drive position in which said head (105) co-operates with said second count wheel (120), said cam means (108) being secured to said fixed tubular element (104) and disposed without significant friction against said inner annular surface (118) of said drive tongue (114) to force the head (115) of said tongue (114) into its drive position whenever said first count wheel (110) has performed a complete revolution about said axis of rotation (103).

21. A counter device according to claim 20, in which said second count wheel (120) includes a set of teeth (121) extending circumferentially about said fixed axis of rotation (103) and directed inwardly, said set of teeth (121) being disposed radially outside said drive tongue (114) of said first drive wheel (110) in such a manner that in its drive position said head (115) of the tongue (114) engages in one of the teeth of said set of teeth (121) to drive said second count wheel (120) in rotation about said fixed axis of rotation (103).

22. A counter device according to claim 1, in which the first and second count wheels (10, 110; 20, 120) include display means on their respective outer peripheral surfaces (16, 116; 26, 126).

\* \* \* \* \*